(12) United States Patent
Kato

(10) Patent No.: US 9,958,668 B2
(45) Date of Patent: May 1, 2018

(54) IMAGE PICKUP UNIT

(71) Applicant: OLYMPUS CORPORATION, Hachioji-shi, Tokyo (JP)

(72) Inventor: Takayuki Kato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/670,853

(22) Filed: Aug. 7, 2017

(65) Prior Publication Data

US 2017/0336620 A1 Nov. 23, 2017

Related U.S. Application Data

(63) Continuation of application No. PCT/JP2016/064714, filed on May 18, 2016.

(30) Foreign Application Priority Data

Jun. 1, 2015 (JP) ................................. 2015-111605

(51) Int. Cl.
*A62B 1/04* (2006.01)
*G02B 23/24* (2006.01)
(Continued)

(52) U.S. Cl.
CPC ......... *G02B 23/2407* (2013.01); *G02B 7/105* (2013.01); *G02B 7/28* (2013.01); *G02B 13/04* (2013.01); *G03B 3/06* (2013.01)

(58) Field of Classification Search
CPC ...... G02B 23/2407; G02B 7/28; G02B 13/04; G02B 7/105; G02B 23/243; G03B 3/06; H04N 2005/2255; A61B 1/00096
(Continued)

(56) References Cited

U.S. PATENT DOCUMENTS 4,398,811 A 8/1983 Nishioka et al.
6,831,693 B1 12/2004 Sunaga
(Continued)

FOREIGN PATENT DOCUMENTS

JP 52088387 U 7/1977
JP 56009712 A 1/1981
(Continued)

OTHER PUBLICATIONS

Decision to Grant a Patent dated Apr. 12, 2017 issued in counterpart Japanese Application No. 2016-561875.
(Continued)

*Primary Examiner* — Jared Walker

(57) ABSTRACT

There is provided an image pickup unit which is capable of achieving a focused image of a favorable depth of field while changing a visual field direction of observation.
An image pickup unit, comprises a front group which includes a prism that can be rotated for changing a visual field direction, and a rear group which includes a lens group and an image pickup element, wherein the image pickup unit includes a prism rotating section which rotates the prism for changing the visual field direction, and a focusing section which does not change a focused range, as an angle of visual field direction with respect to a longitudinal direction of the image pickup unit becomes smaller than a specific angle, and which moves the focused range toward a near-point side, as an angle of visual field direction with respect to the longitudinal direction of the image pickup unit becomes larger than the specific angle, in accordance with a rotation of the prism, and the focusing section, in a case in which the specific angle is not smaller than 30°, moves the focused range toward the near-point side.

3 Claims, 7 Drawing Sheets

(51) Int. Cl.
    *G02B 13/04* (2006.01)
    *G02B 7/105* (2006.01)
    *G02B 7/28* (2006.01)
    *G03B 3/06* (2006.01)
(58) Field of Classification Search
    USPC .......................................................... 348/65
    See application file for complete search history.

(56) References Cited

U.S. PATENT DOCUMENTS

2005/0234294 A1  10/2005  Saadat et al.
2013/0044361 A1   2/2013  Katakura
2013/0070072 A1   3/2013  Honda

FOREIGN PATENT DOCUMENTS

| JP | 06027389 A | 2/1994 |
|---|---|---|
| JP | 06245903 A | 9/1994 |
| JP | 07236610 A | 9/1995 |
| JP | 11125773 A | 5/1999 |
| JP | 2001128038 A | 5/2001 |
| JP | 2007532240 A | 11/2007 |
| JP | 2008289545 A | 12/2008 |
| JP | 5372261 B2 | 12/2013 |
| WO | 2012081349 A1 | 6/2012 |
| WO | 2012132598 A1 | 10/2012 |

OTHER PUBLICATIONS

International Search Report (ISR) and Written Opinion dated Aug. 16, 2016 issued in International Application No. PCT/JP2016/064714.

Japanese Office Action dated Jan. 11, 2017 issued in counterpart Japanese Application No. 2016-561875.

International Preliminary Report on Patentability (and English translation thereof) dated Dec. 14, 2017 issued in International Application No. PCT/JP2016/064714.

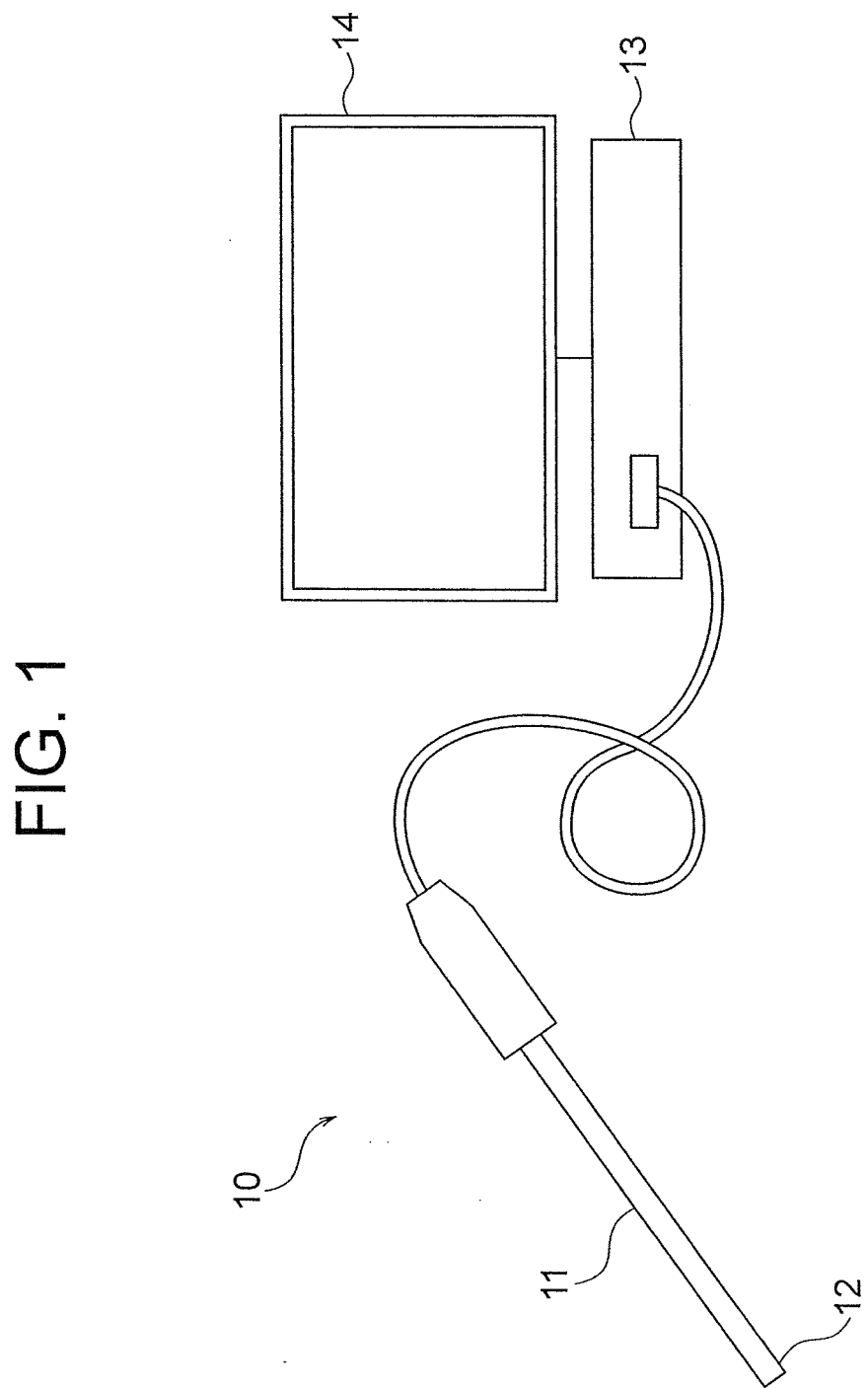

IMAGE PICKUP UNIT

CROSS-REFERENCE TO RELATED APPLICATION

The present application is a continuation application of PCT/JP2016/064714 filed on May 18, 2016 which is based upon and claims the benefit of priority from Japanese Patent Application No. 2015-111605 filed on Jun. 1, 2015; the entire contents of which are incorporated herein by reference.

BACKGROUND OF THE INVENTION

Field of the Invention

The present invention related to an image pickup unit, and particularly to an image pickup unit which is suitable for an endoscope.

Description of the Related Art

An endoscope in which a visual field direction of the endoscope is changed by changing a direction of a front-end surface by making osculate or rotate a mirror or a prism disposed at a front-end portion of the endoscope has hitherto been known (Refer to Japanese Patent Application Laid-open Publication No. Hei 6-245903 and Japanese Patent No. 5372261 Publication for example).

SUMMARY OF THE INVENTION

The present invention provides the following means. According to an aspect of the present invention, an image pickup unit, comprises a front group which includes a prism that can be rotated for changing a visual field direction, and a rear group which includes a lens group and an image pickup element, wherein the image pickup unit includes a prism rotating section which rotates the prism for changing the visual field direction, and a focusing section which does not change a focused range, as an angle of visual field direction with respect to a longitudinal direction of the image pickup unit becomes smaller than a specific angle, and which moves the focused range toward a near-point side, as an angle of visual field direction with respect to the longitudinal direction of the image pickup unit becomes larger than the specific angle, in accordance with a rotation of the prism, and the focusing section, in a case in which the specific angle is not smaller than 30°, moves the focused range toward the near-point side.

BRIEF DESCRIPTION OF THE DRAWINGS

FIG. 1 is a diagram showing an overall arrangement of an endoscope apparatus having an image pickup unit according to an embodiment of the present invention;

DETAILED DESCRIPTION OF THE INVENTION

Figure 2A:
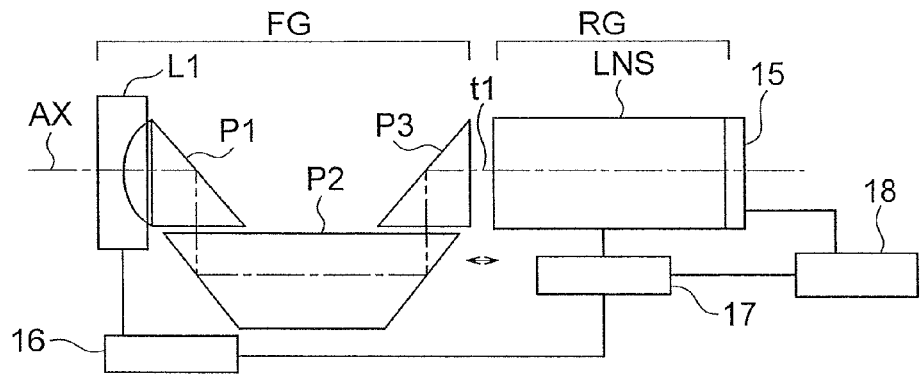
FIG. 2A is a diagram showing a schematic arrangement of an image pickup unit according to a first embodiment of the present invention.

An image pickup unit according to the present invention will be described below by using the accompanying diagrams.

Reasons for and effects of adopting such arrangement for image pickup units according to embodiments of the present invention will be described below by using the accompanying diagrams. However, the present invention is not restricted to the embodiments described below.

FIG. 1 shows a schematic arrangement of an endoscope apparatus 10 having an image pickup unit according to a first embodiment of the present invention. The image pickup unit to be described later has been built-in in a front-end portion 12 of a video endoscope 11. An image signal from the image pickup unit is output to a camera control unit 13 via a universal cord. Moreover, a monitor 14 displays an image that has been picked up.

First Embodiment

Figure 2B:
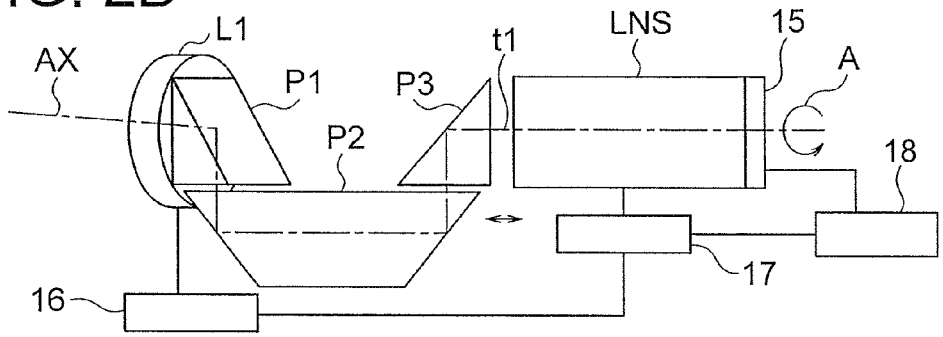
FIG. 2B is another diagram showing a schematic arrangement of the image pickup unit according to the first embodiment of the present invention.
Figure 2C:
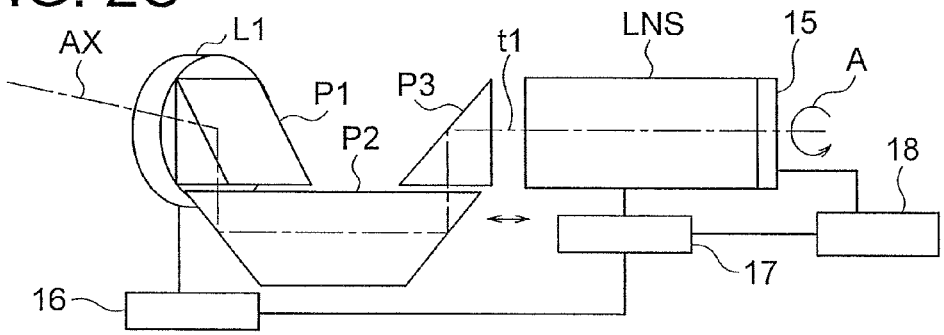
FIG. 2C is still another diagram showing a schematic arrangement of the image pickup unit according to the first embodiment of the present invention.
Figure 2D:
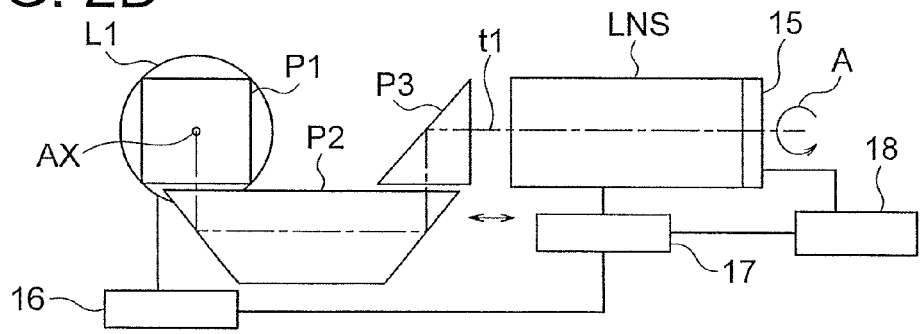
FIG. 2D is still another diagram showing a schematic arrangement of the image pickup unit according to the first embodiment of the present invention.

Each of FIG. 2A, FIG. 2B, FIG. 2C, and FIG. 2D is a diagram showing an arrangement of an image pickup unit according the embodiment of the present invention. FIG. 2A indicates an arrangement when an angle of rotation of a visual field direction is 0°. FIG. 2B indicates an arrangement when the angle of rotation of the visual field direction is 30°. FIG. 2C indicates an arrangement when the angle of rotation of the visual field direction is 60°. FIG. 2D indicates an arrangement when the angle of rotation of the visual field direction is 90°.

The image pickup unit includes a front group FG which includes prisms P1, P2, and P3 which can be rotated for changing the visual field direction, and a rear group RG which includes a lens group LNS and an image pickup element 15. In the diagrams, the lens group LNS, for convenience, is depicted as a plane parallel plate, but has a lens element having a refractive power not less than 1. Moreover, a prism rotating section 16 rotates the prism P1 for changing the visual field direction. A focusing section 17 moves a focused range toward a near-point side, as an angle of visual field direction with respect to a longitudinal direction of the image pickup unit becomes larger than a specific angle, in accordance with the rotation of the prism P1.

The front group FG includes in order from an object side, a lens L1, a right-angle prism P1, a trapezoidal prism P2, and a right-angle prism P3. The prism rotating section 16 rotates the lens L1 and the right-angle prism 91 integrally, with respect to the trapezoidal prism P2.

The focusing section 17 moves the focused range toward the near-point side when the angle through which the lens L1 and the right-angle prism P1 are rotated is not smaller than a specific angle such as 30°.

In the present embodiment, the focusing section 17 changes an air space t1 between the right-angle prism P3 and an integrated body of the image pickup element 15 and the lens group LNS in the rear group RG, in accordance with the angle through which the lens L1 and the right-angle prism P1 are rotated.

Figure 3A:
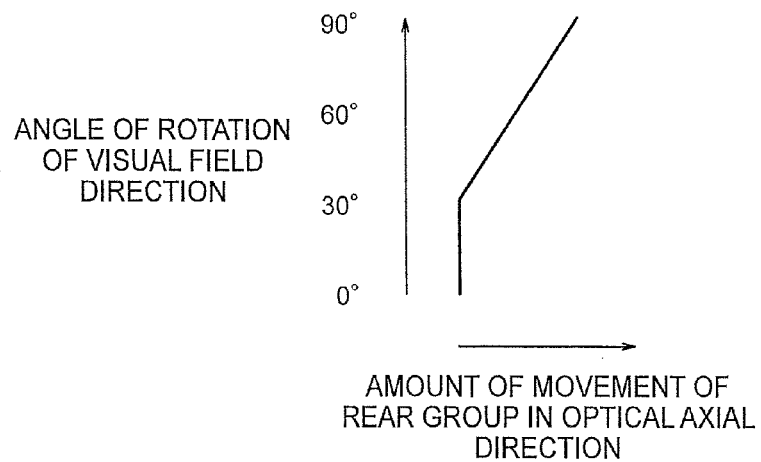
FIG. 3A is a diagram showing an amount of movement of a rear group of the image pickup unit according to the first embodiment of the present invention.

FIG. 3A is a diagram showing a relationship between an amount of movement of the rear group RG in a direction along an optical axis AX and an angle of rotation of the visual field direction of the prism P1. For the angle of rotation of the visual field direction of the prism P1 from 0° up to 30°, the air space t1 is constant. Moreover, for the angle of rotation of the visual field direction of the prism P1 between 30° to 90°, the air space t1 increases linearly.

Figure 3B:
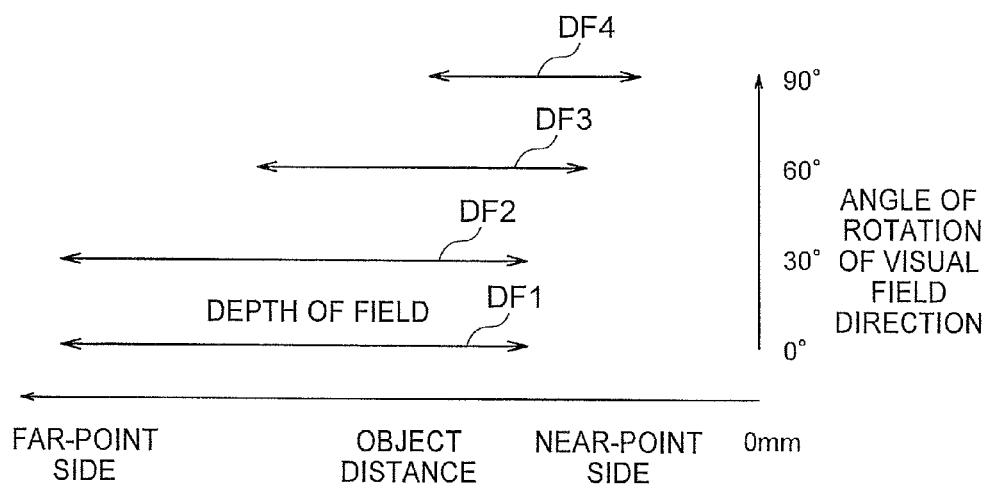
FIG. 3B is a diagram showing a relationship between an angle of rotation of a visual field direction of the image pickup unit according to the first embodiment of the present invention and a depth of field.

FIG. 3B is a diagram showing a relationship between an object distance and the angle of rotation of the visual field direction of the prism P1. For the angle of rotation of the visual field direction of the prism P1 from 0° up to 30°, a depth of field DF1 is constant. For the angle of rotation of the visual field direction of the prism P1 between 30° to 90°, the depth of field becomes smaller in order of DF2, DF3, and DF4 while shifting the focusing position toward the near-point direction. Accordingly, it is possible to achieve the depth of field appropriate to the visual field of view.

In the present embodiment, the focusing section moves the lens group LNS and the image pickup element 15 of the rear group RG along the optical axis AX. Apart from this, the focusing section can also move a specific lens in the lens group LNS of the rear group RG along the optical axis AX.

Moreover, a rotational driving section 18 rotates the lens group LNS and the image pickup element 15 in the rear group RG around the optical axis AX as shown by an arrow A to cancel rotation of an image in the image pickup element 15 generated due to the rotation of the prism P1. Accordingly, it is possible to cancel the rotation of an image due to the rotation of the prism P1.

Second Embodiment

Figure 4A:
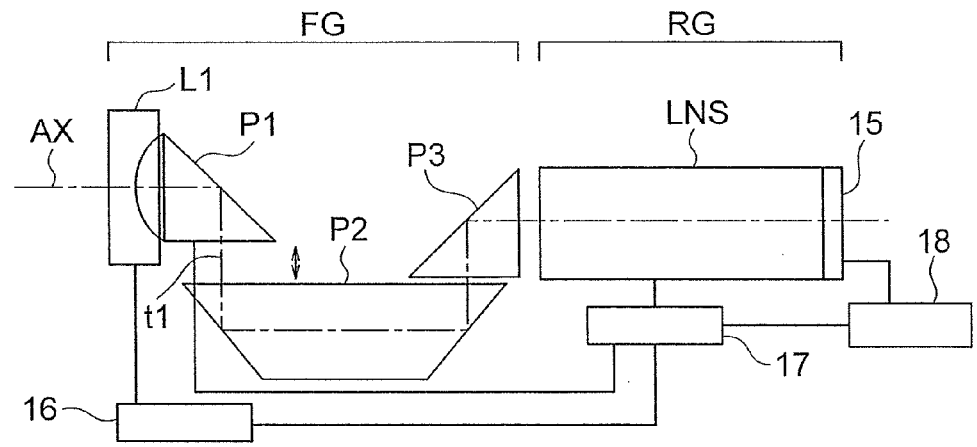
FIG. 4A is a diagram showing a schematic arrangement of an image pickup unit according to a second embodiment of the present invention.
Figure 4B:
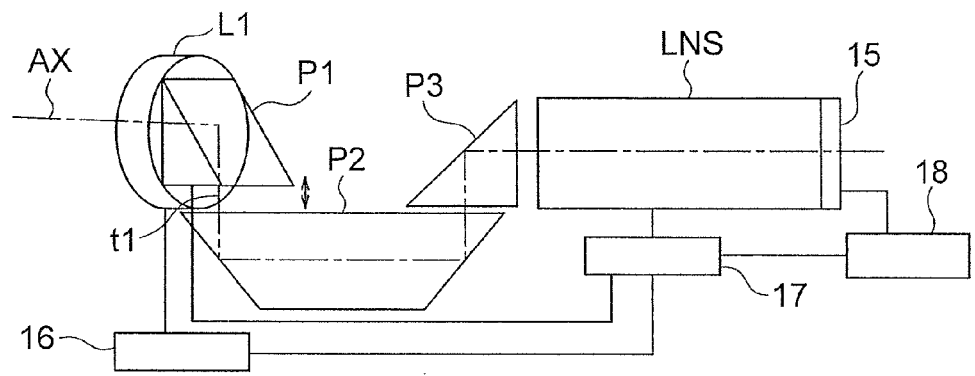
FIG. 4B is another diagram showing a schematic arrangement of the image pickup unit according to the second embodiment of the present invention.
Figure 4C:
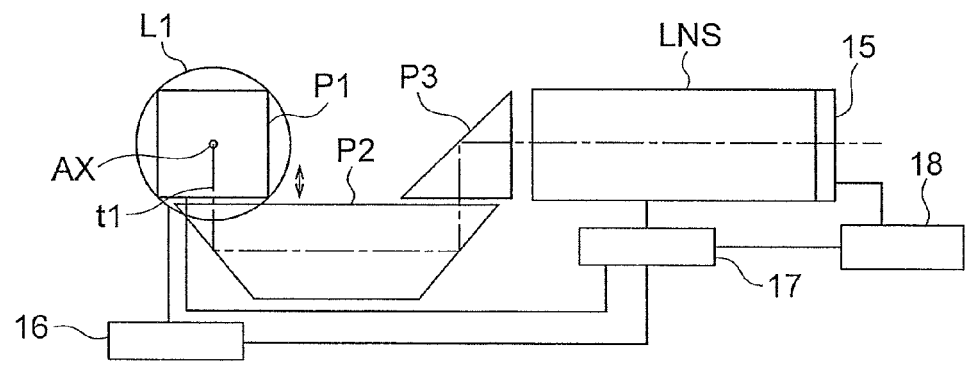
FIG. 4C is still another diagram showing a schematic arrangement of the image pickup unit according to the second embodiment of the present invention.

Each of FIG. 4A, FIG. 4B, and FIG. 4C is a diagram showing an arrangement of an image pickup unit according to a second embodiment of the present invention. FIG. 4A indicates an arrangement when an angle of rotation of a visual field direction is 0°. FIG. 4B indicates an arrangement when the angle of rotation of the visual field direction is 45°. FIG. 4C indicates an arrangement when the angle of rotation of the visual field direction is 90°. Same reference numerals are assigned to components which are same as in the first embodiment, and repetitive description thereof is omitted.

Similarly as in the first embodiment, the focusing section 17 moves the focused range toward the near-point side when the angle through which the lens L1 and the right-angle prism P1 are rotated is not smaller than the specific angle such as 30°.

In the present embodiment, the focusing section 17 changes the air space t1 between the right-angle prism P1 and the trapezoidal prism P2 in the front group FG, in accordance with the angle through which the lens L1 and the right-angle prism P1 are rotated.

Example 1

Figure 5:
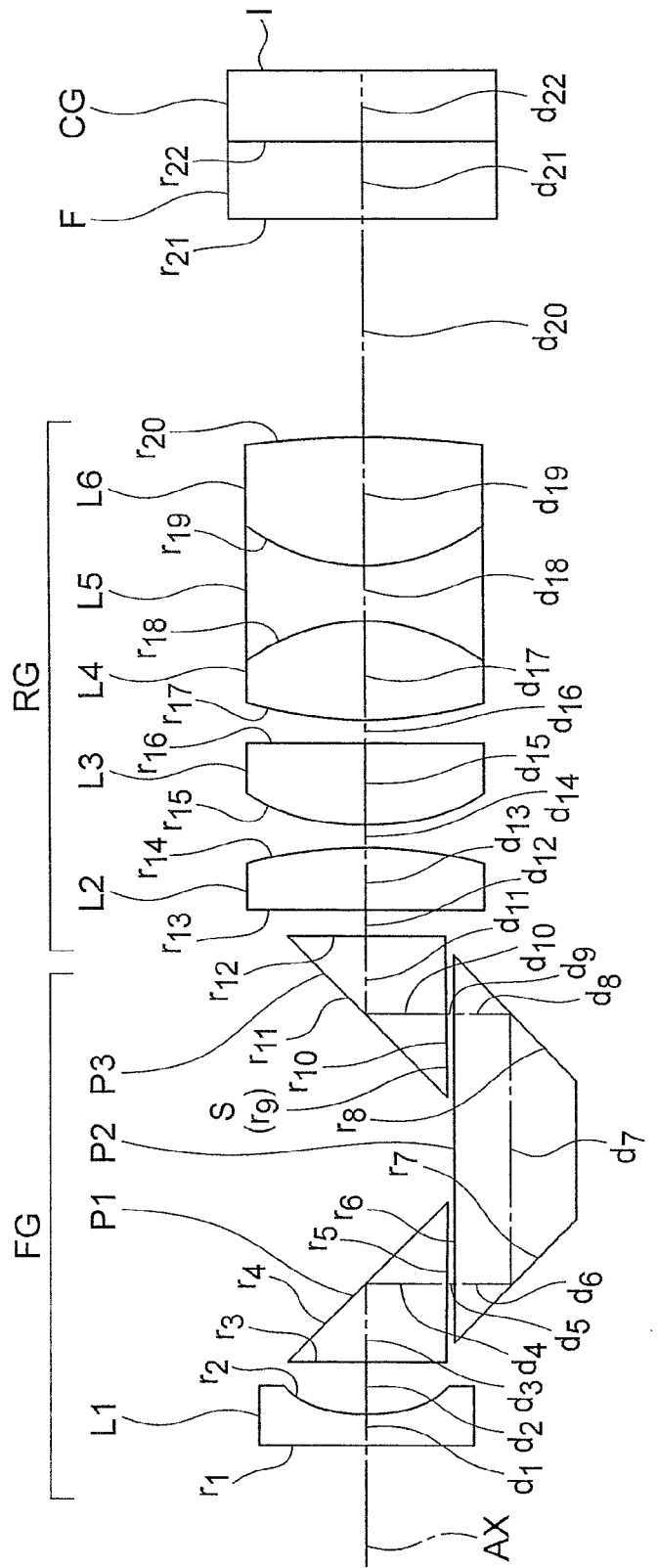
FIG. 5 is a cross-sectional view showing an arrangement of an image pickup unit according to an example 1.

Next, an image pickup unit according to an example 1 of the present invention will be described below. FIG. 5 is a cross-sectional view of the image pickup unit according to the present example.

The image pickup unit of the present example includes in order from an object side, a front group FG which includes a prism that can be rotated for changing the visual field direction, an aperture stops, and a rear group RG which includes a lens group and an image pickup element.

The front group FG includes in order from the object side, a planoconcave negative lens L1 having a concave surface directed toward an image side, a right-angle prism P1, a trapezoidal prism P2, and a right-angle prism P3. The rear group RG includes in order from the object side, a planoconvex positive lens L2 having a convex surface directed toward the image side, a biconvex positive lens L3, a biconvex positive lens L4, a biconcave negative lens L5, and a biconvex positive lens L6. Here, the biconvex positive lens L4, the biconcave negative lens L5, and the biconvex positive lens L6 are cemented.

Moreover, a plane parallel plate F and a plane parallel plate CG are disposed on the image side of the rear group RG. The plane parallel plate F is a filter having a coating applied thereon for cutting off specific wavelengths such as 1060 nm of YAG (Yttrium Aluminum Garnet) laser and 810 nm of semiconductor laser, or an infrared region. In the present example, a distance between the right-angle prism P3 and the planoconvex positive lens L2 can be varied for focusing.

Example 2

Figure 6:
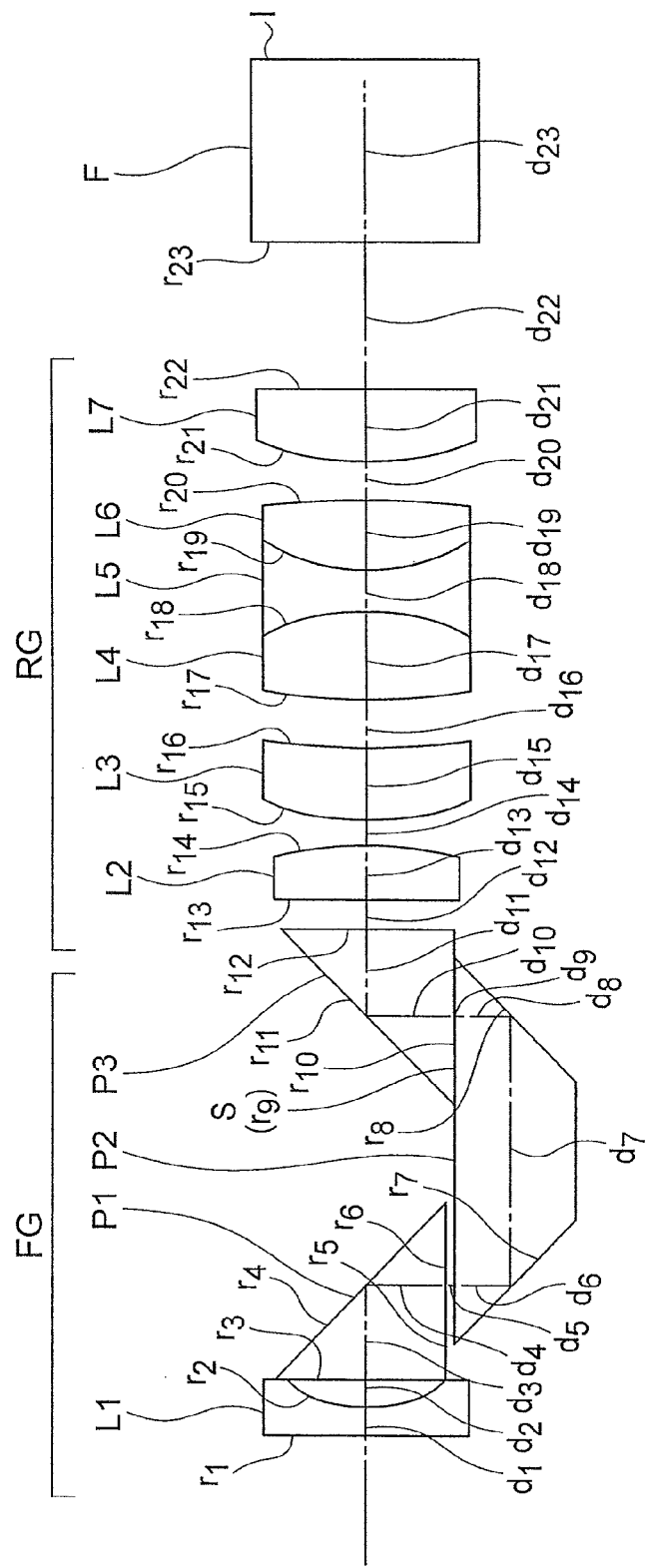
FIG. 6 is a cross-sectional view showing an arrangement of an image pickup unit according to an example 2.

Next, an image pickup unit according to an example 2 of the present invention will be described below. FIG. 6 is a cross-sectional view of the image pickup unit according to the present example.

The image pickup unit of the present example includes in order from an object side, a front group FG which includes a prism that can be rotated for changing the visual field direction, an aperture stop S, and a rear group RG which includes a lens group and an image pickup element.

The front group FG includes in order from the object side, a planoconcave negative lens L1 having a concave surface directed toward an image side, a right-angle prism P1, a trapezoidal prism P2, and a right-angle prism P3. The rear group RG includes in order from the object side, a planoconvex positive lens L2 having a convex surface directed toward the image side, a positive meniscus lens L3 having a convex surface directed toward the object side, a biconvex positive lens L4, a biconcave negative lens L5, a biconvex positive lens L6, and a convexoplane positive lens L7 having a convex surface directed toward the object side. Here, the biconvex positive lens L4, the biconcave negative lens L5, and the biconvex positive lens L6 are cemented.

Moreover, a plane parallel plate F is disposed on the image side of the rear group RG. The plane parallel plate F is a filter having a coating applied thereon for cutting off specific wavelengths such as 1060 nm of YAG laser and 810 nm of semiconductor laser, or an infrared region. In the present example, the positive meniscus lens L3 moves for focusing.

Example 3

Figure 7:
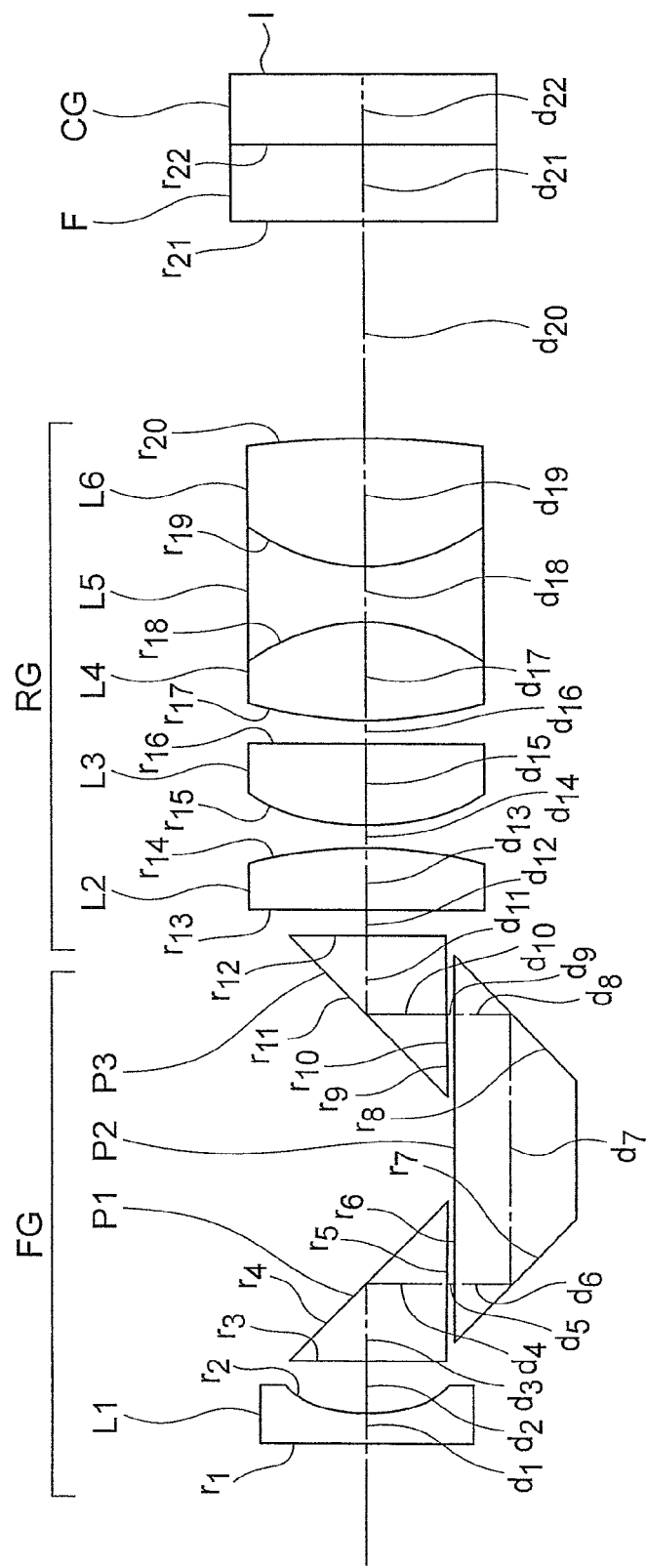
FIG. 7 is a cross-sectional view showing an arrangement of an image pickup unit according to an example 3.

Next, an image pickup unit according to an example 3 of the present invention will be described below. FIG. 7 is a cross-sectional view of the image pickup unit according to the present example.

The image pickup unit of the present example includes in order from an object side, a front group FG which includes a prism that can be rotated for changing the visual field direction, an aperture stop S, and a rear group RG which includes a lens group and an image pickup element.

The front group FG includes in order from the object side, a planoconcave negative lens L1 having a concave surface directed toward an image side, a right-angle prism P1, a trapezoidal prism P2, and a right-angle prism P3. The rear group RG includes in order from the object side, a plano-convex positive lens L2 having a convex surface directed toward the image side, a biconvex positive lens L3, a biconvex positive lens L4, a biconcave negative lens L5, and a biconvex positive lens L6. Here, the biconvex positive lens L4, the biconcave negative lens L5, and the biconvex positive lens L6 are cemented.

Moreover, a plane parallel plate F and a plane parallel plate CG are disposed on the image side of the rear group RG. The plane parallel plate F is a filter having a coating applied thereon for cutting off specific wavelengths such as 1060 nm of YAG laser and 810 nm of semiconductor laser, or an infrared region. In the present example, a distance between the right-angle prism P1 and the trapezoidal prism P2 can be varied for focusing.

Numerical data of each example is shown below. Regarding symbols, r denotes a radius of curvature of each surface, d denotes an air space or a thickness of each optical member, $n_e$ denotes a refractive index of each optical member for an e-line, and $v_e$ denotes Abbe's number for each optical member for the e-line.

Example 1

| (Unit mm) | | | | |
|---|---|---|---|---|
| Surface data | | | | |
| Surface no. | r | d | ne | ve |
| 1 | ∞ | 0.425 | 2.01169 | 28.07 |
| 2 | 1.923 | 0.68 | | |
| 3 | ∞ | 1.15 | 2.01169 | 28.07 |
| 4 | ∞ | 1.15 | 2.01169 | 28.07 |
| 5 | ∞ | 0.07 | | |
| 6 | ∞ | 0.852 | 2.01169 | 28.07 |
| 7 | ∞ | 3.551 | 2.01169 | 28.07 |
| 8 | ∞ | 0.852 | 2.01169 | 28.07 |
| 9 (Stop) | ∞ | 0.07 | | |
| 10 | ∞ | 1.15 | 2.01169 | 28.07 |
| 11 | ∞ | 1.15 | 2.01169 | 28.07 |
| 12 | ∞ | t1 (Variable) | | |
| 13 | ∞ | 0.852 | 1.81264 | 25.22 |
| 14 | −6.712 | 0.298 | | |
| 15 | 3.205 | 1.136 | 1.5343 | 48.55 |
| 16 | −42.59 | 0.327 | | |
| 17 | 6.791 | 1.307 | 1.69979 | 55.31 |
| 18 | −2.73 | 0.781 | 2.01169 | 28.07 |
| 19 | 2.73 | 1.705 | 1.48915 | 70.04 |
| 20 | −17.764 | 3.26 | | |
| 21 | ∞ | 0.8 | 1.51825 | 63.93 |
| 22 | ∞ | 0.8 | 1.61641 | 49.91 |
| Image plane | ∞ | | | |

| Various data | | | |
|---|---|---|---|
| Best object distance (mm) | 50 | 36 | 24 |
| Near-point object distance (mm) | 30.0 | 24.2 | 18.0 |
| Far-point object distance (mm) | 142.0 | 68.4 | 35.5 |
| d12(t1) | 0.355 | 0.385 | 0.43 |
| Diameter φ of aperture stop | 1.25 | | |

Example 2

| (Unit mm) | | | | |
|---|---|---|---|---|
| Surface data | | | | |
| Surface no. | r | d | ne | ve |
| 1 | ∞ | 0.5 | 2.01169 | 28.27 |
| 2 | 2.782 | 0.648 | | |
| 3 | ∞ | 1.73 | 2.01169 | 28.27 |
| 4 | ∞ | 1.605 | 2.01169 | 28.27 |
| 5 | ∞ | 0.25 | | |
| 6 | ∞ | 1.235 | 2.01169 | 28.27 |
| 7 | ∞ | 5.56 | 2.01169 | 28.27 |
| 8 | ∞ | 1.235 | 2.01169 | 28.27 |
| 9 (Stop) | ∞ | 0.0 | | |
| 10 | ∞ | 1.85 | 2.01169 | 28.27 |
| 11 | ∞ | 1.73 | 2.01169 | 28.27 |
| 12 | ∞ | 0.74 | | |
| 13 | ∞ | 1.1 | 1.85504 | 23.78 |
| 14 | −9.25 | t1 (Variable) | | |
| 15 | 5.535 | 1.495 | 1.59143 | 61.14 |
| 16 | 11.916 | t2 (Variable) | | |
| 17 | 10.56 | 1.816 | 1.51977 | 52.43 |
| 18 | −5.4988 | 0.877 | 1.79192 | 25.68 |
| 19 | 4.29 | 1.384 | 1.48915 | 70.23 |
| 20 | −40.418 | 0.775 | | |
| 21 | 6.045 | 1.5 | 1.48915 | 70.23 |
| 22 | ∞ | 2.86 | | |
| 23 | ∞ | 4 | 1.51825 | 64.14 |
| Image plane | ∞ | | | |

| Various data | | | |
|---|---|---|---|
| Best object distance (mm) | 50 | 36 | 24 |
| Near-point object distance (mm) | 31.8 | 25.3 | 18.5 |
| Far-point object distance (mm) | 110.8 | 60.7 | 33.6 |
| d14(t1) | 0.605 | 0.54 | 0.425 |
| d16(t2) | 0.976 | 1.041 | 1.156 |
| Diameter φ of aperture stop | 1.32 | | |

Example 3

| (Unit mm) | | | | |
|---|---|---|---|---|
| Surface data | | | | |
| Surface no. | r | d | ne | ve |
| 1 | ∞ | 0.425 | 2.01169 | 28.07 |
| 2 | 1.923 | 0.68 | | |
| 3 | ∞ | 1.15 | 2.01169 | 28.07 |
| 4 | ∞ | 1.15 | 2.01169 | 28.07 |

-continued (Unit mm)

| | | | | |
|---|---|---|---|---|
| 5 | ∞ | t1 (Variable) | | |
| 6 | ∞ | 0.852 | 2.01169 | 28.07 |
| 7 | ∞ | 3.551 | 2.01169 | 28.07 |
| 8 | ∞ | 0.852 | 2.01169 | 28.07 |
| 9 (Stop) | ∞ | 0.07 | | |
| 10 | ∞ | 1.15 | 2.01169 | 28.07 |
| 11 | ∞ | 1.15 | 2.01169 | 28.07 |
| 12 | ∞ | 0.355 | | |
| 13 | ∞ | 0.852 | 1.81264 | 25.22 |
| 14 | −6.712 | 0.298 | | |
| 15 | 3.205 | 1.136 | 1.5343 | 48.55 |
| 16 | −42.59 | 0.327 | | |
| 17 | 6.791 | 1.307 | 1.69979 | 55.31 |
| 18 | −2.73 | 0.781 | 2.01169 | 28.07 |
| 19 | 2.73 | 1.705 | 1.48915 | 70.04 |
| 20 | −17.764 | 3.26 | | |
| 21 | ∞ | 0.8 | 1.51825 | 63.93 |
| 22 | ∞ | 0.8 | 1.61641 | 49.91 |
| Image plane | ∞ | | | |

Various data

| | | | |
|---|---|---|---|
| Best object distance (mm) | 50 | 36 | 24 |
| Near-point object distance (mm) | 30.0 | 24.2 | 18.0 |
| Far-point object distance (mm) | 142.0 | 68.4 | 35.5 |
| d5(t1) | 0.07 | 0.095 | 0.135 |
| Diameter φ of aperture stop | 1.25 | | |

Various embodiment of the present invention have been described above. However, the present invention is not limited to the embodiments described above, and an embodiment in which the arrangements of abovementioned embodiments are combined appropriately without departing from the scope of the present invention also falls under the category of the present invention.

The present invention shows an effect that it is possible to provide an image pickup unit which is capable of achieving a focused image of a favorable depth of field while changing a visual field direction of observation.

As described above, the present invention is useful for an image pickup unit which is capable of achieving a focused image of a favorable depth of field while changing a visual field direction of observation.

(Note)

An invention with the following arrangement is derived from the abovementioned examples.

(Appended Mode 1)

An endoscope apparatus comprising the image pickup unit according to one of the first embodiment and the second embodiment.

What is claimed is:

1. An image pickup unit, comprising:
   a front group which includes a prism that can be rotated for changing a visual field direction; and
   a rear group which includes a lens group and an image pickup element, wherein
   the image pickup unit includes a prism rotating section which rotates the prism for changing the visual field direction, and a focusing section which does not change a focused range, as an angle of visual field direction with respect to a longitudinal direction of the image pickup unit becomes smaller than a specific angle, and which moves the focused range toward a near-point side, as an angle of visual field direction with respect to the longitudinal direction of the image pickup unit becomes larger than the specific angle, in accordance with a rotation of the prism, and
   the focusing section, in a case in which the specific angle is not smaller than 30°, moves the focused range toward the near-point side.

2. The image pickup unit according to claim 1, wherein the focusing section moves one of the prism in the front group, or the lens group and the image pickup element in the rear group, or a specific lens in the lens group in the rear group, along an optical axis.

3. The image pickup unit according to claim 1, wherein the image pickup unit includes a rotational driving section which rotates the lens group and the image pickup element in the rear group to cancel an image rotation in the image pickup element generated due to the rotation of the prism, with the optical axis as a center of rotation.

* * * * *